United States Patent [19]

McCollum, III. et al.

[11] Patent Number: 4,979,979

[45] Date of Patent: Dec. 25, 1990

[54] HERBICIDAL COMPOSITION

[75] Inventors: William A. McCollum, III., Elkton, Md.; Emil W. Shen, Newark; Robert D. Wysong, Wilmington, both of Del.

[73] Assignee: E. I. Du Pont de Nemours and Company, Wilmington, Del.

[21] Appl. No.: 352,444

[22] Filed: May 16, 1989

Related U.S. Application Data

[63] Continuation-in-part of Ser. No. 59,980, Jun. 17, 1987, abandoned.

[51] Int. Cl.$^5$ ............................................. A01N 25/00
[52] U.S. Cl. ..................................... 71/93; 71/DIG. 1
[58] Field of Search ............................... 71/93, DIG. 1

[56] References Cited

U.S. PATENT DOCUMENTS

| | | | |
|---|---|---|---|
| 2,992,090 | 7/1961 | Littler | 71/2.5 |
| 3,849,105 | 11/1974 | Woods | 71/65 |
| 4,172,714 | 10/1979 | Albert | 71/93 |

FOREIGN PATENT DOCUMENTS

| | | |
|---|---|---|
| 1167661 | 5/1984 | Canada . |
| 1502 | 1/1973 | Japan . |
| 33201 | 2/1984 | Japan . |

OTHER PUBLICATIONS

R. S. Scott, N. Z. J. Agr. Res., 13 (1970), 909–920.
Whisenant et al., Proc. West. Soc. Weed Sci., 39 (1986), 73–84.
Bovey et al., Weed Sci., 33 (1985), 551–554.
Barneux et al., Weed Sci., 30 (1982), 668–671.
Meyer et al., Weed Sci., 26 (1978), 444–453.

*Primary Examiner*—Richard L. Raymond
*Assistant Examiner*—Eric J. Kraus

[57] ABSTRACT

A granular particulate herbicidal composition having characteristics that permit it to be effectively applied to the ground aerially.

**13 Cla

HERBICIDAL COMPOSITION

RELATED APPLICATION

This is a continuation-in-part of copending application U.S. Ser. No. 07/059,980 filed June 17, 1987.

BACKGROUND OF THE INVENTION

The invention relates to a granular particulate herbicidal composition with characteristics that permit the application effectively to forests and woodlands aerially with minimum drift.

It is customary to formulate herbicides as water-dispersible compositions which can be readily mixed with water and applied by means of a spraying apparatus. An important class of herbicides which can be applied by this means comprises the symmetrical triazinediones, of which hexazinone, 3-cyclohexyl-6-dimethylamino-1-methyl-s-triazine-2,4(1H,3H)-dione, is the most widely used. Formulations of this herbicide are marketed throughout the world as weed-killing compounds under the trade name Velpar ® (trademark of E. I. du Pont de Nemours and Company, Wilmington, Delaware).

One difficulty with aqueous herbicide formulations generally is that the active ingredient often has limited solubility in the water in which it is dispersed under the conditions of temperature at which the spraying is carried out. Heretofore, this has meant that the spray concentrations of many herbicides had to be limited to below their solubility limits in order to avoid crystallization within the spray apparatus and concomitant plugging of the spray nozzle. Nozzle plugging is most likely to take place when a crystal size of 150μ in any dimension is reached. Such plugging is of significant economic detriment for the reasons that (1) manpower time must be expended to discontinue spraying operations and remove the plugging material and (2) any area sprayed before the plugging is detected and corrected is likely to be covered inadequately. Hexazinone is one of those compounds which, because of its limited solubility in water, frequently incurs plugging when used at concentrations above its solubility limit at temperatures below about 37° C. (98.6° F.). For this reason, liquid spray herbicidal compositions containing hexazinone have been limited to concentrations of about 2-3% by weight of the active ingredient (hexazinone), unless they are heated to raise the solubility limit. Furthermore there is a tendancy for hexazinone to form insoluble trihydrate crystals in cold water even when the concentration is not saturated.

The application of herbicides in granular particulate form does not incur the disadvantage of aqueous formulations provided they can be effectively applied.

U.S. Pat. No. 4,172,714 discloses a dry compactible composition consisting of large pellets or balls, having a volume in the range of about 0.75 to 2.0 cubic centimeters and containing 5 to 25% by weight of a herbicide which includes hexazinone which is useful for aerial application to woodlands. These pellets or balls are advantageous in that they can be produced by dry compaction, are impact and crush resistant while dry and are highly resistant to disintegration in high humidity atmospheres.

Japanese publication No. 59-33201 discloses granules containing 3 to 16 wt % of antimicrobial agents and insecticides as active ingredients for aerial application which are characterized by (1) a particle size of 10-12 mesh, (2) the number of granules per 1 g is 200-350, (3) the percent of particles in which the weight of 1 particle exceeds 5 mg is 10-30%, (4) the percent of particles in which the weight of 1 particle is 2 to 5 mg os 50-85% and (5) the percent of particles in which the weight of 1 particle is less than 2 mg is 5-20%.

U.S. Pat. No. 3,849,105 discloses a granular pesticide that can be applied aerially with minimized drift. There is however, no disclosure of the characteristics of the granules. The only disclosure is of 16 to 20 mesh particles of the carrier.

Japanese Publication No. 48-1502 discloses an agrichemical granule formulation for aerial spreading by helicopter with a rest angle of 35–50%.

Applications which require the herbicide to be in the form of large pellets or balls or other particulate form cannot be effectively applied aerially because of (1) attrition of the particulates by the equipment used to discharge the particulates aerially, (2) drift of the particulates resulting in an ineffective application, and/or (3) inability to achieve control of vegetation.

Where sufficiently large pellets have been used to eliminate drift from aerial applications ineffective biological control of undesired vegetation has resulted. Large pellets or balls may contain too much active ingredient causing injury to desired species or may take too long to break up to effect control of undesired vegetation or may provide inadequate density of ground coverage. Where pellets have met attrition requirements for aerial application the percent of active ingredient has been sufficiently low to make them less attractive economically for control of large areas, e.g., forest or woodlands. Low active ingredient requires reloading more times because of limited capacities of airplanes compared with high percent active ingredients.

SUMMARY OF THE INVENTION

Now herbicidal granular particulate formulations have been discovered for application to forests and wildlands and for industrial weed control with improved application efficiency for the control of undesired vegetation aerially. The granular particulate formulations comprise a herbicide at high concentrations that can be effectively used in forestry applications to control undesired vegetation. The effectiveness of the herbicide in forestry applications is improved by the rapid release of the herbicide from the granular particulate. Thus the granules will have release rates of 55 to 95% of the active ingredient in 4 minutes in the release rate test and thus will provide activity and will effectively control undesired vegetation with minimum rainfall. The granules rapidly disintegrate releasing herbicidal components with minimal rainfall. Applications can be made up to a height of 130 feet, giving a swath width up to 95 feet in up to 10 mph crosswinds. The herbicidal granular particulate formulations have characteristics which permit, when applied aerially, effective applications to the ground where the undesired vegetation is located, said characteristics comprising particulates wherein 95% to 100% by weight (preferably 96% to 100% and more preferably 98% to 100%) have a drop time of from 2 to 35 seconds (preferably 2 to 25 seconds) by the Drop Test and no more than 2% by weight attrition to particles that fall slower than 35 seconds (preferably slower than 25 seconds) by the Drop Test. Attrition is measured by the Attrition Test and drop time by the Drop Test. The granular particulate formulations of the invention can be dispersed aerially without appreciable drift with the achievement of uniform distribution on the ground capable of controlling the growth of undesired vegetation to an acceptable degree. The granular particulates of the invention contain 50–99% by weight herbicide.

More preferred granular particulates are those which have a drop time of 4 to 20 seconds and no more than 2% attrition to particles falling slower than 25 seconds by the Drop Test.

The herbicidal granular particulate compositions of the invention comprise 50–99% by weight of a herbicide selected from hexazinone, mixtures of hexazinone with sulfometuron methyl, and agriculturally suitable salts of sulfometuron methyl with hexazinone wherein at least 95% of the granular particulates by weight have drop times of from 2 to 35 seconds in the Drop Test and attrition of less than 2% by weight to particles having a drop time greater than 35 seconds said composition having a release rate in water of 60–95% by weight of the herbicide in 4 minutes.

Most preferred among the herbicides of the invention is hexazinone. However the granular particulates of the invention may comprise other herbicides.

The granular particulate formulations of the invention allow consistent, predictable distribution with negligible wind drift, while economizing material used and further reducing the number of flights required because the payload contains dry active ingredients in high concentration. Liquid compositions have not only have added weight due to water but also are less concentrated. Other dry compositions are also less concentrated.

The granular particulate of the invention can be made by first blending the powdered, preblended ingredients including the active herbicide. The blended ingredients are then hammermilled, reblended, airmilled to a herbicidally active particle size of 5–25 mm and optionally reblended again. This milled blend is then granulated on a pan (disc) granulator by spraying water onto the powder to form granules. The granules are then dried in a vibrating fluidized bed to produce the particulate of the invention.

In order to ensure proper aerial applications with low drift, the granular particulates of the invention must have the following physical characteristics:

Attrition: no greater than 2% by weight as determined by the Attrition Test

Particle Drop Time: at least 95% by weight of the particles must drop in less than 35 seconds as determined by Drop Test Herbicidal Assay: 50–99% by weight of active herbicide Establishing the actual parameters of size, shape and density for a particulate of the invention that will result in an acceptable drop time, and therefore acceptable field performance, can be done several ways. Typically pan granulation is conducted once formulation ingredients are chosen. Pan granulation operation variables, such as depth, rotation speed and pan angle are selected which will produce a particulate with a characteristic shape and density. The formulation and the pan granulation variables are defined and then the particle size limits are established by sieving a crude pan-granulated product into several fractions of specific narrow mesh size ranges (such as $-8/+10$, $-10/+12$, $-12/+14$) and subjecting the granules from each screen to the Drop Test. At least 95% by weight of the granules must meet the drop time criteria (falling between 2 and 35 seconds). This enables one to find the range of particle size that meets the drop time criteria.

This procedure can be repeated until the full range of particle size is established for acceptable particulate.

The release rate of the herbicide or active ingredient in the case of herbicidal applications is important to the effectiveness thereof. More specifically the rapid release of the active ingredient when the granule is exposed to moisture provides timely, effective biological control without undesirable delays that could otherwise lead to poor biological performance. The present herbicidal granular compositions release the active ingredient rapidly even under mild rainfall conditions.

The granular compositions of the invention generally have release rates in water of 55–95% by weight of the herbicide or the active ingredient in 4 minutes. Preferably said release rate is 60–95%.

RELEASE RATE TEST

Add 800 milliliters ±11 milliliters of distilled or deionized water to a one liter pyrex beaker (4" I D., 15.25" High) and set the stainless steel stirring paddle (3"×13/16") of an adjustable speed stirring motor ½ inch from the bottom of the beaker and adjust speed to 40 RPM ±1 RPM. Add 0.3600 grams ±0.02 grams (record exact weight) of the granular composition and start timing. At 4 minutes using a syringe draw 2 milliliters of solution from 1" below the water surface near the paddle shaft. Transfer the sample to an analytical vial with an acrodisc filter. Assay the sample using the standard hexazinone assay method.

DROP TEST

The Drop Test is an efficient method for determining in the laboratory whether or not a particulate material will meet the deposition requirements for field application. The drop time is determined in a controlled environment and therefore not subject to the outside variations of nature. Drop time limits describing an acceptable product will vary according to type of application, terrain features, nature of surrounding vegetation, meteorological conditions, the height of the applying vehicle above the ground, and the severity of measures needed to control off-target drift of the herbicide. For particular application, such as aerial herbicide application to forestry, drop time limits can be established by testing placebo formulations in the field and correlating acceptable deposition on target with drop times. Once this drop time limit has been identified for a placebo or herbicidal particulate, it will hold true for any product applied in the same manner in that market.

The times in the Drop Test define the general aerodynamic properties of our material, that is, the combined effect of particle size, bulk density, surface features, and shape.

A 2000 mL graduated cylinder, 8 cm in diameter is marked as follows:

(1) one line 5 cm from top rim
(2) second line 12 cm below above mark
(3) last line 25 cm below second mark Light paraffin oil (saybolt viscosity 125/135 @ 100° F., density 0.86–0.87 g/cc @ 25° C.) is poured into the cylinder to a level equal to the top mark. From each portion to be tested 50 particles are randomly selected. One at a time, each particle is placed into the cylinder and allowed to drop 12 cm to reach terminal velocity. Timing begins as the granule passes the second mark and ends as it passes the last mark.

The particulate of the invention must not have an average drop time greater than 35 seconds per 25 cm.

ATTRITION TEST

This test measures the amount of the granular particulate of the invention which when passed through a metering box during aerial application breaks down into dust and/or fine particles having drop times in excess of 35 seconds.

Before conducting this test, the Drop Test is used to determine the particle size range resulting in acceptable drop times. A sample to be evaluated is then screened through U.S. standard screens of sizes that reflect this particle size range until a refined sample weighing at least 300 grams total on all screens is obtained.

To subject the particulate to attrition conditions, the metering box depicted in FIGS. 1, 2 and 3 is employed. The blade and shaft assembly is rotated at 70 revolutions per minute as verified by using a Jaquet hand-held speed indicator.

FIG. 1 is a schematic drawing of the hopper, motor and metering box used for the attrition test. FIG. 2 is a top view thereof and FIG. 3 is a cross section of FIG. 1 through line 3—3.

Referring to FIG. 2, the hopper top opening has dimensions of length L equal 11 inches and width W equal 6 inches and the hopper side is at an angle $\alpha$ of 50°. The bottom opening is $8\frac{1}{2}$ inches$\times\frac{1}{2}$ inch.

Referring now to FIG. 3, a 300 gram sample is poured into the hopper of metering box 1. The sample passes across the rubber flap 3 that is 1/16 inch thick through the counterclockwise rotating blade assembly 4 and is either carried by the blades through another cycle or forced out through the opening 5 in cylinder 6 onto a pretared catch tray 7. The cylinder 6 has an I.D. Of $1\frac{7}{8}''$ the blade clearance with the cylinder 6 is $\frac{1}{4}$ inch. The shaft 8 and blade extend across the hopper 9 inches. The shaft has a diameter of $\frac{3}{4}$ inches and each blade extension from the shaft is 5/16 inch. When the entire sample has passed through the box the metered granules in the catch tray are weighed. The blades subject the particulate to a certain degree of stress or attrition.

Then the metered granules are brushed onto a stack of screens of varying mesh sizes, the largest mesh (smallest openings) giving drop times in excess of 35 seconds and the smallest mesh (largest openings) giving drop times less than 2 seconds and a catch pan. The stack is shaken, and the weight of undersized particulate collected in the catch pan is determined. The percent attrition to particles having drop times above 35 seconds that pass through the smallest openings into the catch pan is calculated by use of the mathematical formula:

$$\%\ \text{Attrition} = \frac{\text{Weight of undersized granules (pan)}}{\text{Total Weight of granules collected in catch tray}} \times 100\%$$

For the hexazinone-containing spheroidal (shape factor 0.9) granules prepared in Formulation Examples 1–3 below, the acceptable drop time range as determined by the Drop Test was found to correspond to particle sizes of U.S. 6–14# (particles that remain on screens of a mesh from 6 to 14). (For a description of "shape factor" see T. Allen, *Particle Size Measurement*, 3rd Ed., Chapman and Hall, New York, 1981, p. 110.) Granules of these Examples smaller than U.S. 14# fell too slowly (drop times > 35 s) in the Drop Test. The desired product cut (in this case, U.S. 6–14#) was obtained by prescreening on a Gilson Sieve Tester #SS-15 for 5 minutes and then subjected to the Attrition Test as described above. A U.S. 14# screen was used in the final screen-catch pan assembly. The % Attrition as calculated by use of the formula above is recorded in Table 2.

HERBICIDAL ASSAY

The amount of hexazinone in the granular particulate can be determined by the method that follows. Other herbicidal assays can be determined by similar procedures.

An acetonitrile solution of a granular sample of the herbicide of the invention, containing an internal standard, is separated by gas chromatography on an analytical column packed with *Chromosorb WHP*. The eluted compounds are detected and quantitated with a flame ionization detector and a digital integrator. A calibration curve (i.e. peak area ratio vs. concentration), prepared from standard hexazinone solutions, is used to determine the amount of hexazinone in the sample.

This method will detect at least 0.8% hexazinone with a relative standard deviation of 1.2%.

BULK DENSITY

The loose bulk density is determined by filling a container of known volume with granules of the particulate in a standard fashion and then weighing the filled container. The bulk density is calculated from the weight of the material and the volume occupied.

The following examples of preparing granular particulates of the invention involve percentages by weight unless otherwise indicated:

EXAMPLE 1

(Formulation 1)

The following powdered raw materials were charged to a ribbon blender:

| | Lbs | % |
|---|---|---|
| technical hexazinone (98% purity) | 400 | 79.6 |
| $\alpha$-lactose monohydrate | 55.23 | 11.0 |
| diisopropylnaphthalene sulfonate, sodium salt | 30.10 | 6.0 |
| polyethoxylated dinonylphenol (150 ethyleneoxide units) | 15.1 | 3.0 |
| sodium stearate | 1.15 | 0.3 |
| sodium alginate | 0.5 | 0.1 |

The ingredients were blended 15 min. and then auger-fed to a no. 2 DH hammermill without a screen for delumping and then reblended in another ribbon blender. This blend was then fed to a 24 in. diameter air mill (ring pressure 80 psi, feed pressure, 25 psi) to yield a premix (average particle size 17 microns). This premix was auger-fed at 1000 lbs./hr. to a 4.5 foot diameter pan (8 inches depth) for granulation under the following conditions: 50° angle, 20 rpm, 81.1 lbs./hr. spray rate of water from two nozzles ($L_2$ and $L_4$ hollow cone type). The resulting damp granules (7.5% moisture) were conveyed to a vibrating dryer with fluidized air (1/16 in. wire-type deck with 0.006 in. opening, 10% free area, 54 sq. ft. total deck area). The dryer was equipped with 4 in. height weirs where the inlet air temperature to the three zones was 120°–140° F. (49°–60° C.) and the air velocity through the deck was 300 ft./min. The emerging partially dried granules (3% moisture) were passed a second time at a rate of 1000 lbs./hr. through a similar dryer and sieved through a stack of vibrating screens to give final semi-spherical product with the properties listed in Table 2 (samples A and B were taken at two different times from the above continuous production run).

EXAMPLES 2 AND 3

The following formulations were prepared following the procedure in Example 1.

EXAMPLE 2

78% technical hexazinone
14.8% lactose
4.0% sodium diisopropyl napthalene sulfonate
0.1% sodium stearate
0.1% sodium alginate
3% polyethoxylated dinonylphenol

EXAMPLE 3

78% technical hexazinone
14.8% Barden clay
3.0% sodium dialkyl napthalene sulfonate (Daxad ® 11G)
4.0% sodium diisopropyl napthalene sulfonate
0.1% sodium stearate
0.1% sodium alginate The physical characteristics of the formulations are shown in Table 2.

TABLE 2

Physical Characteristics of Examples 1 to 3

|  | Example 1 A | Example 1 B | Example 2 | Example 3 |
|---|---|---|---|---|
| % Hexazinone | 77.4 | 76.6 | 77.0 | 77.1 |
| % Moisture | 1.3 | 2.2 | 2.5 | 1.5 |
| Lb/Ft$^3$ Bulk Density | 35.61 | 39.6 | 40.0 | 40.0 |
| Avg. Drop Time/Sec | 13 | 13 | 13 | 14 |
| % Attrition (wt % of particles with a drop time greater than 35 sec.) | 0.7 | 0.7 | 0.1 | 0.2 |

In the formulations of the invention in Examples 1–3, lactose functions as a water soluble binder/diluent and helps rapid release into the soil of the hexazinone herbicide even during low rainfall and allows the formulation to also be used like a conventional dry flowable when mixed with water and sprayed. Barden Clay is a diluent and anticaker which promotes high density for antidrift during aerial application. Sodium diisopropyl napthalene sulfonate is a wetting agent, cobinder, and crystal growth inhibitor which prevents attrition during aging and which prevents nozzle plugging during aqueous applications. Sodium alginate is a binding agent. Daxad ® 11G (sodium dialkyl naphthalene sulfonate) and polyethoxylated dinonyl phenol functions as cobinders/dispersing agents. Sodium stearate is an antifoam for aqueous application.

For treating large areas where the terrain is difficult to reach, aerial applications are the preferred method of applying herbicides. Aerial applications are done at sufficient height above the terrain to avoid obstacles. Specific physical and chemical properties are important in assuring predictably accurate and thus safe and efficacious results. Above and beyond having the requisite biological activity, choosing the proper product parameters not only assures the before-mentioned results but also increases productivity.

Known granular products or liquid products possess low strength and their carriers (such as water) create a major inconvenience due to the weight thereof and are a large cost component of herbicide application.

In addition with respect to liquid applications, it is difficult to control the fine droplets formed as the liquid is released. The released liquid can move off the intended target and cause unwanted damage. Current nonaerial application methods with dry (granule) spreaders can cause attrition or "breaking up" of the dry materials producing small particles which can have as much potential to cause off-target damage as liquid applications and result in a lack of uniform distribution. Lack of uniform distribution can lead to damage to desirable vegetation or lack of control of undesirable vegetation due to irregularities in product rates on the ground.

The granules of the present invention, although advantageously applied in granular form, can be applied by aqueous spraying. The granular particulate of the invention is readily dispersible in water.

There are three key variables to control to get the desired aerodynamic behavior from particles: shape, density, and size. It is a combination of all three factors, not each singly that is important. This invention is directed to granular particulate herbicidal compositions with a combination of properties which permit the granule to be bound together, to be of high enough active strength to be economically viable to the grower, and to be makable in a shape compatible with the density, in a size to get it away from aircraft wake, and of ingredients having characteristics that give a size, attrition resistance, water solubility and active content per particle that is biologically desirable.

The wake of an aircraft flying between 60 and 100 mph, speeds which are typical for agricultural applications by helicopters and fixed wing aircraft, greatly affects the particle parameters needed to maximize deposition on target and get a uniform application across the desired swath width. Particles which do not have the requisite combination of density, size and surface uniformity or relative sphericity can get caught in the aircraft wake or in the wind and be thrown off target, or at a minimum, lead to a non-uniform pattern.

To some extent, adjustments can be made in the positioning of the discharge points of the particles on the aircraft to get them out of the wake. However, other considerations, such as pilot safety, and environmental conditions such as winds may make the necessary changes impractical or impossible.

The simple Drop Test of this invention quickly leads to identification of particles which have the requisite combination of physical parameters when applied from aircraft to give deposition on target and a uniform swath from equipment which is easy for the pilot to use. This test works for formulations of hexazinone and also for any other agricultural formulation which would not be solubilized by the paraffin oil. It eliminates the need to field test a number of prototype formulations, which is very expensive and inefficient to do. The test does not measure size, density or shape alone, but the interaction of all three on a particle. It involves dropping individual particles into a specific liquid and measuring the time to travel a specified interval once terminal velocity in the liquid is achieved. Particles of different size, but common density and shape behave differently. Particles of different density, but common size and shape behave differently. Any particles of different shape, but similar size and density, also are differentiated. These observations in the laboratory test substantiate findings in actual field studies. As a result, it is possible to predict whether a particle will behave satisfactorily when discharged from an aircraft simply by observing whether it has an acceptable drop time in the liquid.

The importance of particle aerodynamics in formulating materials for aerial applications in forestry, wildlands and for industrial weed control can be seen in Tables 3 through 6. The tables demonstrate how particle aerodynamics, as expressed by drop times from the Drop Test are influenced by all three components of size, shape, and density.

In Table 3 four sample materials of varying bulk densities (lb/ft$^3$) available commercially are listed with their corresponding times from the Drop Test. The particles measured were all of the same spherical shape factor of 0.90 and of the same size ($-14/+16$ mesh). As particle density increases so does the speed at which the particles fall.

TABLE 3

The drop times of spherical particles of uniform ($-14/+16$ mesh) size vary with the bulk density.

| Material | Bulk Density (lb/ft$^3$) | Drop Time seconds |
|---|---|---|
| Molecular Sieves | 43. | 15.0 |
| Spike | 34.3 | 62.4 |
| Bladex 90 | 29. | 73.8 |
| Aatrex 9-0 | 26. | 82.8 |

In Table 4 the shape of particles can be seen to influence the rate of fall in the Drop Test. In this table all particles were constructed from the same homogeneous clay material and are of equal weight per particle (0.200 g). All the shapes were designed to pass through a 28 mm opening. The drop times show that particle shape can influence the aerodynamics (expressed as drop time) of particles with a spherical shape having the most rapid descent and a flake having the slowest descent.

TABLE 4

Effects of changing shape on drop time when mesh size (28 mm) and weight (0.200 g) are kept constant.

| Shape | (Avg) Drop Time (sec) |
|---|---|
| Sphere | 3.70 |
| Cube | 4.04 |
| Triangular prism | 4.31 |
| Cluster | 4.29 |
| Cylinder | 4.61 |
| Flake (rectangular plate) | 5.30 |

Table 5 shows that particles made of a homogeneous formulation of hexazinone granules of the invention having a spheroidal shape (shape factor 0.90) and bulk density (38 lb/ft$^3$) will exhibit increasing rates of fall in the drop test as their size is increased.

TABLE 5

Effects of changing size of particles on drop time when density (38 lb/ft$^3$) and shape (spherical) are held constant.
Hexazinone Granular Particulate

| Size (mesh) | (Avg) Drop Time (sec) |
|---|---|
| $-6/+8$ | 12.9 |
| $-12/+14$ | 32.6 |
| $-20/+25$ | 87.4 |

TABLE 5-continued

Effects of changing size of particles on drop time when density (38 lb/ft$^3$) and shape (spherical) are held constant.
Hexazinone Granular Particulate

| Size (mesh) | (Avg) Drop Time (sec) |
|---|---|
| $-35/+40$ | 279.5 |

Table 6 shows that hexazinone particles of a given shape and density, with drop times greater than 35 seconds measured by the Drop Test are significantly displaced by wind, and thereby removed from targeted sites, creating the potential for unwanted herbicidal activity. Poor control of particle size, density and shape and thus the unpredictability of product placement also makes control of uniform distribution a problem. This lack of uniform distribution can be expressed in damage to desirable vegetation. The results are due to irregularities in product rates on the ground. All of these attributes of increased efficiency, uniform distribution, controlling pattern shape and minimizing off-target movement can be accomplished by controlling the combination product parameters that actually determine particle flight characteristics, namely: size, density, shape. Equally important are maintaining these desirable parameters throughout proper formulation, manufacturing, and application methods. The granular particulate of the invention defines those parameters for forestry, wildland and industrial weed control herbicides that will give effective herbicidal activity and maximize application efficiency. This approach differs from traditional herbicide designs which target formulation advantages but do not maximize use advantages.

TABLE 6

EFFECT OF VARYING PARTICLE SIZE ON PARTICLE DROP TIME AND PARTICLE RECOVERY WITHIN 150 FT OF RELEASE POINT (HEXAZINONE PARTICULATE)

| MESH SIZE | SHAPE FACTOR | BULK DENSITY (lb/cu ft) | DROP TEST SECONDS | % RECOVERY |
|---|---|---|---|---|
| $-7/+8$ | .90 | 36 | 16.7 | 95.06 |
| $-10/+12$ | .90 | 36 | 31.3 | 99.62 |
| $-12/+14$ | .90 | 36 | 41.25 | 91.7 |
| $-20/+40$ | .90 | 36 | 279 | 51.0 |
| $-40/+60$ | .90 | 36 | >350 | 0.0 |

The particle parameters of the invention are based on requirements for aerial release from heights up to 130 feet above the terrain in crosswinds up to 10 mph. Granules with the parameters of the invention will when applied under the above stated conditions swaths of greater than 60 feet result in particulate distributions providing efficacious control of undesirable species.

The particulate formulations have characteristics which permit, when applied aerially, effective applications to the ground of any particulate comprising any combination of size, density and surface uniformity or relative sphericity that will impart the proper particle aerodynamics permitting a drop time of 2 to 35 seconds by the Drop Test. Attrition must not cause more than 2% by weight of the particulate formulations of the instant invention to consist of particles having drop times in excess of 35 seconds.

Granular particulates with the characteristics disclosed herein were field tested using the Pattern Analysis System defined below. Products were flown, both in calm and windy conditions, into the wind and cross-wind, to determine how the products which had acceptable flight characteristics related to those which did not.

The Pattern Analysis equipment consists of collectors, balances and computer hardware-software. The collectors consist of 3 rows of 15 collectors with an interval between collectors in a row of 10 feet. Each row is separated from the adjacent row by 20 feet. The collectors are made 3 feet by 3 feet of lightweight rip-stop nylon cloth on a rigid frame. In the Pattern Analysis System the nylon cloth absorbs the impact of the granules as they fall, thereby increasing the "capture" efficiency of the traps. The materials fall to the bottom of the traps and are captured in pre-marked (Location and Test I.D.) graduated tubes.

The tubes are removed after each test and weighed on a gram balance. Each weight and location is entered into a computer where preprogrammed software statistically analyzes the data from each pattern, giving an accounht of deposited rate uniformity and/or variation across the pattern. The software also models the swath to analyze its possible operational results.

During each test, environmental data on wind speeds and direction, temperature and relative humidity is recorded as well as the flight parameters and equipment configurations. True ground speed of the helicopter is indicated by measurement with a MPH radar gun.

The relationship between drop time in the Drop Test and predictability of uniform deposition is important in aerial application, especially since those particles with fast drop times fall away from the wake influences of the aircraft and equipment faster.

Once these physical characteristics were determined, biological trials confirmed that particles with the necessary parameters and having a concentrated amount of material per granule do effectively control undesirable species of plants on wildland sites. A hexazinone formulation of 75% active material with a drop time range in the Drop Test of 2-20 seconds was aerially applied on 10 sites in the southern United States to determine biological efficacy of products with desirable flight characteristics. Operational flight methods were based on data acquired from field trials using the Du Pont Granular Pattern analysis system.

The sites were chosen to give the widest representation of soil, topography and undesirable vegetation present on forestry sites. Each site consisted of plots 300 feet×400 feet separated by 50 feet plowed or pushed boundary lines surrounding each plot. Fifty specimens of the targeted pest species were tagged and numbered before the treatments. The plots were treated at a rate which represented the prescribed hexazinone rate for the soil type and species present for currently used liquid and overcoated dilute (10%) granules. The delivery equipment was calibrated and checked before each application, and an on-ground check was made at one site using the Pattern Analysis System to confirm accurate and uniform deposition as predicted in the pre-trial analysis. All applications were made by a Bell 47B or 47G helicopter.

The product was applied on all sites at a 130 foot release height while flying multiple swaths at 60 mph in back and forth manner at 95 foot widths centerline (under the aircraft) to centerline. For consistency, all tracts were flown in winds under 5 mph. The results shown in table 8 confirmed that herbicidal activity can be maintained while addressing product physical parameters that optimize its aerial application use pattern.

TABLE 8
SUMMARY OF HEXAZINONE RESULTS ON NINE TESTS SITES
% DEFOLIATION BY SPECIES

| TREATMENTS | HEXAZINONE APPLICATION RATE (LBS/ACRE) | RED OAK | WHITE OAK | SWEET GUM | WINGED ELM | HICKORY | DOGWOOD | BLACK GUM | SASSAFRAS | WINGED SUMAC | LOBIOLLY PINE | HERBACEOUS CONTROL |
|---|---|---|---|---|---|---|---|---|---|---|---|---|
| 1. Evaluated 76 DAT[1] | | | | | | | | | | | | |
| Hexazinone | 3.0 | 99 | 99 | 99 | 99 | 90 | 99 | 99.3 | — | — | 5 | 95 |
| Hexazinone | 3.5 | 99 | 99 | 99 | 99 | 16.7 | 88 | 94.5 | — | — | 0 | 97.7 |
| 2. Evaluated 87 DAT | | | | | | | | | | | | |
| Hexazinone | 3.0 | 88.3 | — | 85 | 95 | 71.7 | 26.7 | .75 | — | — | 0 | 78 |
| Hexazinone | 4.0 | 99.3 | — | 99 | 99.5 | 99 | 99 | 20 | — | — | 5 | 99.3 |
| 3. Evaluated 89 DAT | | | | | | | | | | | | |
| Hexazinone | 3.0 | 96 | 95 | 87.5 | 99.7 | — | — | 74.7 | — | — | 0 | 68.3 |
| Hexazinone | 3.5 | 97.7 | 94.7 | 96.3 | 99 | 45.0 | 85 | 32.5 | — | — | 0 | 56.7 |
| 4. Evaluated 86 DAT | | | | | | | | | | | | |
| Hexazinone | 3.0 | 98.3 | 99.7 | 94.7 | 100 | 41.7 | 90.0 | 87.5 | — | — | 1.7 | 90.0 |
| Hexazinone | 3.5 | 96.3 | 98.0 | 96.3 | 99.3 | 48.3 | 85.0 | 62.0 | — | — | 4.3 | 81.7 |
| 5. Evaluated 86 DAT | | | | | | | | | | | | |
| Hexazinone | 3.0 | 98 | 99.3 | 99.3 | — | 82 | 99.3 | 59.5 | — | — | — | 97.7 |
| Hexazinone | 4.0 | 100 | 100 | 100 | — | 99 | 97.7 | 97.0 | — | — | 0 | 90 |
| 6. Evaluated 104 DAT | | | | | | | | | | | | |
| Hexazinone | 3.0 | 95 | 91 | — | — | 80 | 88 | — | 75 | — | 1.0 | — |
| Hexazinone | 4.0 | 95 | 96 | — | — | 84 | 95 | — | .75 | — | 9.0 | — |
| 7. Evaluated 94 DAT | | | | | | | | | | | | |
| Hexazinone | 3.0 | 89 | — | 74 | — | 82 | 88 | — | 97 | 100 | 5 | — |
| Hexazinone | 4.0 | 95 | — | 89 | — | — | — | — | 100 | 92 | 70 | — |
| 8. Evaluated 110 DAT | | | | | | | | | | | | |
| Hexazinone | 3.0 | 96 | 98 | — | 90 | 88 | 90 | — | — | — | — | — |
| Hexazinone | 4.0 | 98 | 98 | 90 | 95 | — | 96 | — | — | — | — | — |
| 9. Evaluated 92 DAT | | | | | | | | | | | | |
| Hexazinone | 2.5 | 94 | 97 | — | — | — | — | — | 84 | — | — | — |
| Hexazinone | 3.0 | 89 | 100 | — | — | — | — | — | 90 | — | — | — |

[1]DAT - DAYS AFTER TREATMENT
[2]HERBACEOUS CONTROL - GENERAL CONTROL OF FOREST SITE GROUND COVERS

The dry particulate herbicidal composition of the invention can include one or more other biologically active compounds to form a multicomponent herbicide giving an even broader spectrum of effective agricultural protection. In particular, it may be advantageous to prepare the dry particulate with a combination of herbicides.

Examples of other biologically active compounds that may be incorporated into the dry particulate with the active herbicides described above include:

*Bacillus thuringiensis*

Avermectin B

| | Chemical Name |
|---|---|
| Trade Name or Code Number | |
| DPX-L5300 | 2-[[N-(4-methoxy-6-methyl-1,3,5-triazine-2-yl)-N-methylaminocarbonyl]-aminosulfonyl]benzoic acid, methyl ester |
| PPG-1013 | 5-(2-chloro-4-(trifluoromethyl)phenoxy)-2-nitroacetophenone oxime-O-acetic acid, methyl ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl-p-toluic acid, methyl ester |
| Common Name | |
| acifluorfen | 5-[2-chloro-4-(trifluoromethyl)phenoxy]-2-nitrobenzoic acid |
| acrolein | acrolein |
| alachlor | 2-chloro-2',6'-diethyl-N-(methoxymethyl)-acetanilide |
| ametryn | 2-(ethylamino)-4-(isopropy)amino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropyl-amino)-s-triazine |
| barban | 4-chloro-2-butynyl m-chlorocarbanilate |
| benefin | N-butyl-N-ethyl-α,α,α-trifluoro-2,6-dinitro-p-toluidine |
| bensulide | O,O-diisopropyl phosphorodithioate S-ester with N-(2-mercaptoethyl)-benzenesulfonamide |
| bentazon | 3-isopropyl-1H-2,1,3-benzothiadiazin-4(3H)-one 2,2-dioxide |
| benzipram | 3,5-dimethyl-N-(1-methylethyl)-N-(phenylmethyl)benzamide |
| benzoylprop | N-benzoyl-N-(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N-(butoxymethyl)-2-chloro-2',6'-diethylacetanilide |
| butam | 2,2-dimethyl-N-(1-methylethyl)-N-(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| butylate | S-ethyl-diisobutylthiocarbamate |
| cacodylic acid | hydroxydimethylarsine oxide |
| carbetamide | D-N-ethyllactamide carbanilate (ester) |
| CDAA | N-N-diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |

-continued

| | Chemical Name |
|---|---|
| chlorsulfuron | 2-chloro-N-[(4-methoxy-6-methyl-1,3,5-triazin-2-yl)aminocarbonyl]benzene-sulfonamide |
| chlortoluron | N'-(3-chloro-4-methylphenyl-N',N'-dimethylurea |
| cinmethylin | exo-1-methyl-4-(1-methylethyl)-2-[(2-methylphenyl)methoxy]-7-oxabicyclo-[2.2.1]heptane |
| cisanilide | cis-2,5-dimethyl-N-phenyl-1-pyrrolidine-carboxamide |
| CMA | calcium methanearsonate |
| cyanazine | 2-[[4-chloro-6-(ethylamino)-s-triazin-2-yl]amino]-2-methylpropionitrile |
| cycloate | S-ethyl N-ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H-1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S-(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]-propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^4$,$N^4$-diethyl-α,α,α-trifluoro-3,5-dinitrotoluene-2,4-diamine |
| dinoseb | 2-sec-butyl-4,6-dinitrophenol |
| diphenamide | N,N-dimethyl-2,2-diphenylacetamide |
| dipropetryn | 2-(ethylthio)-4,6-bis(isopropylamino)-s-triazine |
| diquat | 6,7-dihydrodipyrido[1,2-α:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N-ethyl-N-(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyloxy)phenoxy)propanoate |
| fenuron | 1,1-dimethyl-3-phenylurea |
| fenuron TCA | 1,1-dimethyl-3-phenylurea mono(trichloroacetate) |
| flamprop | N-benzoyl-N-(3-chloro-4-fluorophenyl)-DL-alanine |
| fluchloralin | N-(2-chloroethyl)-2,6-dinitro-N-propyl-4-(trifluoromethyl)aniline |
| fluometuron | 1,1-dimethyl-3-(α,α,α-trifluoro-m-tolyl)-urea |
| fluorodifen | p-nitrophenyl α,α,α-trifluoro-2-nitro-p-tolyl ether |
| fluridone | 1-methyl-3-phenyl-5-[3-(trifluoromethyl)phenyl]-4(1H)-pyridinone |
| fomesafen | 5-(2-chloro-4-trifluoromethylphenoxy)-N-methylsulfonyl-2-nitrobenzamide |
| fosamine | ethyl hydrogen (aminocarbonyl)phosphonate |
| glyphosate | N-(phosphonomethyl)glycine |
| haloxyfop methyl | 2-(4-(3-chloro-5-trifluoromethylpyridin-2-yloxy)phenoxy)propanoic acid, methyl ester |

| Chemical Name | |
|---|---|
| hexaflurate | potassium hexafluoroarsenate |
| hexazinone | 3-cyclohexyl-6-(dimethylamino)-1-methyl-1,3,5-triazine-2,4(1H,3H)-dione |
| imazapyr | 2-(4,5-dihydro-4-methyl-4-(1-methylethyl)-5-oxo-1H-imidazol-2-yl]-3-pyridinecarboxylic acid and agriculturally suitable salts thereof such as 1:1 with 2-propanamine |
| imazaquin | 2-(4,5-dihydro-4-methyl-4-(1-methylethyl)-5-oxo-1H-imidazol-2-yl)-3-quinolinecarboxylic acid |
| imazethapyr | 2-[4,5-dihydro-4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 2,6-dinitro-N,N-dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H-cyclopentapyrimidine-2,4(3H,5H)-dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N-[(2,4-dimethyl-5-[[(trifluoromethyl)sulfonyl]amino]phenyl]acetamide |
| methalpropalin | N-(2-methyl-2-propenyl)-2,6-dinitro-N-propyl-4-(trifluoromethyl)benzenamide |
| methabenzthiazuron | 1,3-dimethyl-3-(2-benzothiazolyl)urea |
| metham | sodium methyldithiocarbamate |
| methazole | 2-(3,4-dichlorophenyl)-4-methyl-1,2,4-oxadiazolidine-3,5-dione |
| methoxuron | N'-(3-chloro-4-methoxyphenyl)N,N-dimethylurea |
| metolachlor | 2-chloro-N-(2-ethyl-6-methylphenyl)-N-(2-methoxy-1-methylethyl)acetamide |
| metribuzin | 4-amino-6-tert-butyl-3-(methylthio)-as-triazine-5(4H)-one |
| metsulfuron methyl | methyl 2-[[[(4-methoxy-6-methyl-1,3,5-triazin-2-yl)aminocarbonyl]aminosulfonyl]benzoate |
| molinate | S-ethyl hexahydro-1H-azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-(α-naphthoxy)-N,N-diethylpropionamide |
| naptalam | N-1-naphthylphthalamic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-(α,α,α-trifluoro-m-tolyl)-3(2H)-pyridazinone |
| oryzalin | 3,4-dinitro-N,N-dipropylsulfanilamide |
| oxadiazon | 2-tert-butyl-4-dichloro-5-isopropoxyphenyl)$^{\Delta 2}$-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethy 1-4,4'-bipyridinium ion |
| PBA | chlorinated benzoic acid |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N-(cyclopropylmethyl)-α,α,α-trifluoro-2,6-dinitro-N-propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro N-(1,1-dimethyl-2-propynyl)benzamide |
| propachlor | 2-chloro-N-isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| quinofop ethyl | 2-[4-(6-chloroquinoxalin-2-yloxy)phenoxypropanoic acid, ethyl ester |
| secbumeton | N-ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| sulfometuron methyl | methyl 2-[[[[(4,6-dimethyl-2-pyrimidinyl)amino]carbonyl]amino]sulfonyl]benzoate |
| supriox | 2-[1-(2,5-dimethylphenyl)ethylsulfonyl]-pyridine-N-oxide |
| TCA | trichloroacetic acid |
| tebuthiuron | N-[5-(1,1-dimethylethyl)-1,3,4-thiadiazol-2-yl]-N,N'-dimethylurea |
| terbacil | 3-tert-butyl-5-chloro-6-methyluracil |
| terbuchlor | N-(butoxymethyl)-2-chloro-N-[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert)-4-(ethylamino)-6-(methylthio)-s-triazine |
| tetrafluron | N,N-dimethyl-N'-[3-(1,1,2,2-tetrafluoroethoxy)phenyl]urea |
| thiameturon methyl | 3-[[[(4-methoxy-6-methyl-1,3,5-triazin-2-yl)aminocarbonyl]aminosulfonyl]-2-thiophenecarboxylic acid, methyl ester |
| thiobencarb | S-[(4-chlorophenyl)methyl] diethylcarbamothioate |
| triallate | S-(2,3,3-trichloroallyl)diisopropylthiocarbamate |
| trifluralin | α,α,α-trifluoro-2,6-dinitro-N,N-propyl-p-toluidine |
| trimeturon | 1-(p-chlorophenyl)-2,3,3-trimethylpseudourea |
| vernolate | S-propyl dipropylthiocarbamate |
| | ethyl 5-[2-chloro-4-(trifluoromethyl)phenoxy]-2-nitrobenzoic acid |
| 2,3,6-TBA[b] | 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |

Agriculturally suitable salts of the above listed biologically active compounds may also be included in the dry particulate herbicidal composition of the invention.

The granulate particulate formulations of this invention can significantly increase the efficiency of aerial applications of herbicides on forestry, wildlands, and industrial weed control sites. An example of that efficiency is the quantity of land that can be treated per load on a given aircraft. A Bell 206B helicopter, such as those commonly used in the applications of herbicides cited in this invention, can safely carry an average load of 500 lbs of material. A helicopter with one full load of conventional liquid product would contain enough material for treating 12 acres. In applications of a low strength granule of 10% hexazinone such as those currently used in forestry, a Bell 206 can safely carry enough material to treat 17 acres per load. In field test of a high strength (75%) granule with the properties outlined in this invention, the same aircraft can carry enough material to treat 125 acres in one load. This considerable increase in efficiency translates to much more time applying product and less time loading and ferrying aircraft. The increased efficiencies of this invention have a considerable impact in reducing users' application cost.

What is claimed is:

1. A herbicidal granular particulate composition comprising 50-99% by weight of hexazinone wherein at least 95% of the granular particulates by weight have drop times of from 2 to 35 seconds in the Drop Test and attrition of less than 2% by weight to particles having a drop time greater than 35 seconds said composition having a release rate in water of 55-95% by weight of the herbicide in 4 minutes.

2. The particulate composition of claim 1 wherein at least 96 wt % of the particles have drop times of from 2 to 35 seconds.

3. The particulate composition of claim 1 wherein at least 98 wt % of the particles have drop times of from 2 to 35 seconds.

4. The particulate composition of claim 1 wherein at least 95% of the granular particles by weight have drop times of 4 to 20 seconds and attrition of less than 2% by weight to particles having a drop time of greater than 25 seconds.

5. The particulate composition of claim 1 having an attrition of less than 2% by weight to particles having a drop time greater than 25 seconds.

6. The composition of claim 1 which has a release rate of 60-95%.

7. A method of controlling the growth of undesired vegetation by applying aerially to the locus to be controlled an effective amount of the composition of claim 1.

8. A method of controlling the growth of undesired vegetation by applying aerially to the locus to be controlled an effective amount of the composition of claim 2.

9. A method of controlling the growth of undesired vegetation by applying aerially to the locus to be controlled an effective amount of the composition of claim 3.

10. A method of controlling the growth of undesired vegetation by applying aerially to the locus to be controlled an effective amount of the composition claim 4.

11. A method of controlling the growth of undesired vegetation by applying aerially to the locus to be controlled an effective amount of the composition of claim 5.

12. A method of controlling the growth of undesired vegetation by applying aerially to the locus to be controlled an effective amount of the composition of claim 6.

13. A method of controlling the growth of undesired vegetation by applying aerially to the locus to be controlled an effective amount of the composition of claim 1 from an altitude of up to 130 feet giving a swath width of up to 95 feet in up to 10 MPH cross winds.

* * * * *